United States Patent [19]

Ishida et al.

[11] 4,072,667
[45] Feb. 7, 1978

[54] PROCESS FOR RECOVERING MICROBIAL CELLULAR PROTEINS

[75] Inventors: Masahiko Ishida; Yoshitaka Oguri; Norio Shimizu; Tadashi Muroi, all of Hitachi, Japan

[73] Assignee: Hitachi, Ltd., Japan

[21] Appl. No.: 525,928

[22] Filed: Nov. 21, 1974

Related U.S. Application Data

[63] Continuation of Ser. No. 316,896, Dec. 20, 1972, abandoned.

[30] Foreign Application Priority Data

Dec. 22, 1971 Japan .................................. 46-103683

[51] Int. Cl.$^2$ ................................................. A23J 1/18
[52] U.S. Cl. .................................................. 260/112 R
[58] Field of Search ..................................... 260/112 R

[56] References Cited

U.S. PATENT DOCUMENTS

| 3,121,665 | 2/1964 | Parfentjev | 260/112 X |
| 3,157,635 | 11/1964 | Tanaka et al. | 260/112 X |
| 3,562,289 | 2/1971 | Battista et al. | 260/112 X |
| 3,642,978 | 2/1972 | Ogawa | 260/115 |
| 3,725,075 | 4/1973 | Muroi et al. | 260/112 X |

OTHER PUBLICATIONS

Biochemical J., vol. 56, 1954, pp. 529–543, Margoliash.
The Proteins, vol. III, 1965, pp. 14–27, Neurath.
Methods in Enzymology, vol. XXII, 1971, Jakoby, pp. 273–286.
Biochemical J., vol. 59, 1955, pp. 543–552, Boardman et al.
Kunin, "Ion Exchange Resins", 2nd ed., John Wiley & Sons, New York, p. 92.
Calmon and Kressman, "Ion Exchangers in Organic and Biochemistry", Interscience Pub., New York, 1957, p. 124.

*Primary Examiner*—Paul R. Michl
*Attorney, Agent, or Firm*—Craig & Antonelli

[57] ABSTRACT

Proteins contained in microbial cells, for example, cells of petroleum-assimilable yeast, are separated and purified by extracting proteins from microbial cells, treating the resulting extract solution with a cation exchanger, treating said cation exchanger containing the adsorbed proteins with a volatile basic substance in the presence of water thereby to desorb or elute the adsorbed proteins, removing said basic substance dissolved in the resulting eluate by evaporation, and then concentrating the eluate thereby to obtain the dissolved proteins.

35 Claims, 1 Drawing Figure

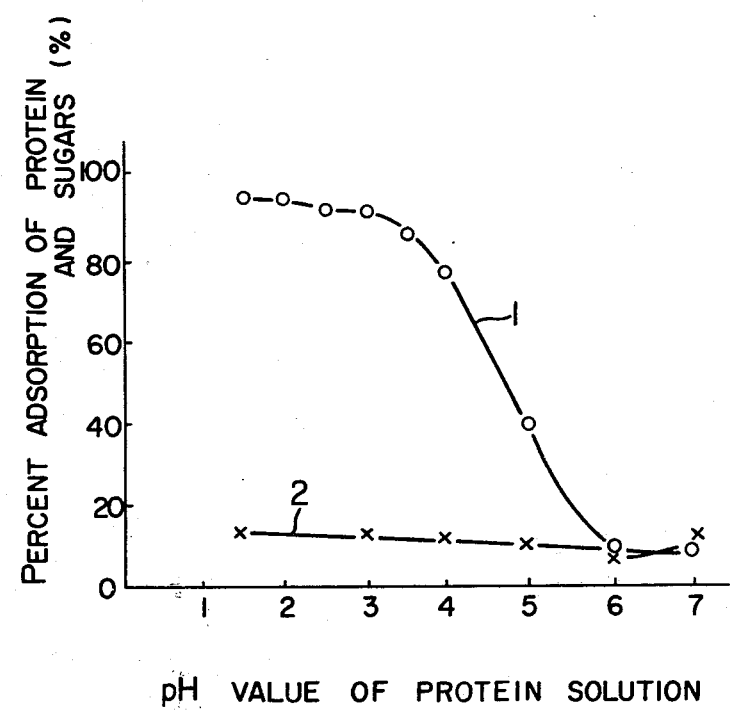

PROCESS FOR RECOVERING MICROBIAL CELLULAR PROTEINS

This is a continuation, of application Ser. No. 316,896 filed Dec. 20, 1972 now abandoned.

It is known that microbial cells such as cells of yeast, etc. contain a considerably large amount of proteins, and their proteins have considerably higher nutritive value than the vegetable protein. Recently, the microbial cellular proteins have been regarded as quantitatively as well as qualitatively important protein source, and utilization of proteins of some microbial cell, for example, proteins of petroleum-assimilable microorganisms, as an animal feed or fish feed have been already taken into consideration. Soon such kind of animal feeds or fish feeds will be started to be produced in a mass projection scale. When these microbial cellular proteins are indirectly converted to edible proteins through the animal feeds or fish feeds, only about 10% by weight of the proteins given as the feeds is converted to animal meat or fish meat, and thus the utilization efficiency of the proteins is considerably low. Furthermore, a long period of time as well as a broad ground area is necessary for breeding or growing animals or fishes and therefore the production efficiency is very low in this case, as compared with that of said microbial cellular proteins. Therefore, it is most effective and important to utilize the microbial cellular proteins directly as food. However, the microbial cells generally have strong and tough cell walls and are hardly digestable. Furthermore, the microbial cellular proteins cannot be taken as food, as they are, because of their peculiar disagreeable smells and coloring.

The microbial cellular proteins do not consist of simple proteins, almost all of which has similar physico-chemical properties, such as vegetable proteins, for example, soybean protein, etc. or milk protein, but the microbial cellular proteins inside the cells are present in a state like a mixture of various kinds of proteins having different physico-chemical properties, even if the strains are identical with one another. Therefore, it is very difficult to separate and purify the microbial cellular proteins in high yield and with high purity, and consequently any economical process for separating and purifying the microbial cellular proteins has not been so far available. It is therefore an important task to separate and purify the microbial cellular protein economically in high yield and with high purity.

Heretofore, a few processes have been proposed for purifying proteins from microbial cells, but it has been impossible, even in these processes, to separate and purify, on the whole, all of various kinds of proteins having different properties economically in high yield and with high purity from an extract solution obtained by subjecting the microbial cells to an extraction treatment with an alkali solution or urea solution of a high concentration.

Taking into account these situations, the present inventors have made studies to find a new process for economically separating and purifying, on the whole, the proteins that have been so far unseparable by the conventional precipitation method.

An object of the present invention is to provide a process for separating and purifying all the proteins contained in the microbial cells in high yield and with high purity.

Another object of the present invention is to provide a process for separating and purifying proteins that are dissolved at a low concentration in a solution, from which most of proteins have been separated by the precipitation method, in high yield and with high purity.

Other object of the present invention is to provide an economical process for separating and purifying proteins from the microbial cells.

Further object of the present invention is to provide a process for separating and purifying proteins in a state free from disagreeable smells and coloring.

Still further objects of the present invention will be apparent from the following description.

The present invention is characterized by a process which comprises a step of contacting a solution of microbial cellular proteins with a strong cation exchanger thereby to adsorb the proteins onto said cation exchanger at a pH of 4.5 or less, a step of contacting said cation exchanger that has adsorbed the protein with a volatile basic substance in the presence of water thereby to desorb or elute the proteins, and a step of removing said volatile basic substance in the resulting protein eluate by evaporation and concentrating the eluate to separate the proteins.

FIGURE is a graph showing a relation between pH value of a protein solution and percent adsorption of the proteins and sugars at the adsorption by strong cation exchanger.

DETAILED EXPLANATION OF THE EMBODIMENTS

According to the present invention, dissolved proteins can be effectively separated and purified. Further, the proteins that are not separable by the precipitation method, such as isoelectric point method, etc. and the proteins in a dilute protein solution can be very effectively separated and purified in the present invention.

The present inventors have confirmed that, when a strong cation exchanger is contacted with a solution of microbial cellular proteins in a specific pH range, said cation exchanger can effectively adsorb the dissolved proteins. Taking this finding into consideration, the present inventors have further found that proteins adsorbed on said cation exchanger can be simply and effectively recovered by treating the cation exchanger with a volatile basic substance.

The FIGURE shows a relation between pH values of the following sample protein solution, the percent adsorption of proteins and percent adsorption of sugars, when a strongly acidic, sulfonic acid-type, cross-linked dextran as the strong cation exchanger is used for adsorption of a protein solution of *Candida lipolytica*, a kind of petroleum-utilizing yeasts, namely petroyeasts, as the sample solution of microbial cellular proteins. As is apparent from the FIGURE, about 60% of the initially dissolved proteins is adsorbed at a pH of about 4.5, as shown by the curve 1, and more than 90% thereof is adsorbed at a pH of about 3.5. On the other hand, the percent adsorption of sugars is as low as about 10% of the initially dissolved sugars, irrespective of the pH, as shown by the curve 2. That is, the amount of sugars mixed into the purified proteins is considerably small in terms of their absolute amount, and this fact is very favourable for the purification of proteins. The foregoing tendencies are almost likewise observed when other strong cation exchangers and other microbial cellular proteins are used. For example, in the case of weakly acidic ion exchangers, only very limited protein components such as basic proteins can be adsorbed, among the microbial cellular proteins, even if a pH is changed at the adsorption, and all of the microbial cellular proteins cannot be adsorbed on the whole.

The pH of a solution of microbial cellular proteins can be adjusted by adding an acid such as hydrochloric acid, etc. to the solution, in the case of alkali-extracted protein solution or neutral solution. If the protein solution is obtained by acid extraction, or if the pH of the solution is below 4.5 by the action of organic acids contained in the cells, it is, of course, not necessary to add the acid to the solution. When the pH is adjusted to about 4.2 in the present invention, an isoelectric point precipitation takes place, and a considerable amount of the proteins precipitates. However, in the present invention, the adsorption can be carried out with the cation exchanger, after said precipitates have been separated, or while said precipitates are retained as they are. In any case, the presence of said precipitates does not give any unfavourable influence at all upon the succeeding steps including the adsorption step. The pH adjustment can be carried out before or while the solution is contacted with the cation exchanger. Hydrochloric acid is most practical with respect to cost as the acid for the pH adjustment, but acetic acid and other organic acids can be also used for the pH adjustment.

The cation exchanger used in the present invention has strongly acidic dissociation groups. Particularly preferable ion exchanger has the following properties. Three-dimensional networks of the ion exchanger are expanded by swelling when the ion exchanger is dipped in water, whereby the polymer proteins can be permeated far into the ion exchanger, and sufficiently bonded and adsorbed on exchange groups, for example, sulfonic acid groups inside the ion exchanger. In some ion exchanger, the degree of swelling in water is small, the networks fail to be expanded, and only low molecular weight substances are adsorbed, but high molecular weight substances such as proteins are adsorbed only on its surfaces. In the present invention, such cation exchanger of non-swelling type is not used. Examples of the preferable cation exchangers include strong cation exchangers, namely sulfonated or phospholyrated cellulose, sulfonated or phosphorylated cross-linked dextran and sulfonated or phosphorylated polyacryamide, etc. Any state of cation exchangers, for example, granular state, film state or liquid state of the cation exchanger, can be used, but the granular state is most practical, because each operation of separation from the solution, washing and regeneration can be easily carried out after the adsorption of the proteins in the case of the granular state.

The adsorption by the cation exchanger can be carried out by contacting a protein solution with said cation exchanger according to various methods, for example, (1) a method comprising filling the cation exchanger in a column, passing a protein solution through the column, separating and removing the resulting filtrate or passing filtrate through the column once again or with several repetitions, and separating and removing the depleted filtrate, or (2) a method comprising mixing the protein solution with the cation exchanger in a vessel, and separating the cation exchanger, which has adsorbed the protein, from the depleted solution after a proper stirring.

In the present invention, the proteins adsorbed on the cation exchanger are treated with a volatile basic substance in the presence of water, and desorbed or eluted thereby. The volatile basic substance is used, because it plays an important role in making the operation of the final step simple, efficient and economical. That is, when an acid or salt solution is used to desorb or elute the proteins from the cation exchanger, there occur separation and development, that is, chromatography, between the respective components of proteins, and not only a very large amount of the eluting agent is necessary, but also the eluted fractions are considerably diluted. Furthermore, it is necessary to remove the acid or salt from the eluted liquid to recover the proteins, and in the case of an alkali metal salt such as sodium chloride, alkali metal ions are adsorbed on the cation exchanger, and consequently a large amount of a regenerating agent such as a strong acid or strong alkali is required for the regeneration of said cation exchanger. Therefore, the basic substance is used. However, in the case of involatile strong alkali such as sodium hydroxide or potassium hydroxide, an operation of removing such alkali from the protein solution eluted becomes complicated, and inefficient. Furthermore, since such alkali is strongly bonded to the cation exchanger, while replacing the proteins, a large amount of a regenerating agent is necessary for the regeneration of said cation exchanger, and the process becomes economically disadvantageous. These disadvantages can be eliminated by using a volatile basic substance. Finally, the volatile basic substance can be simply removed by drying under reduced pressure or by heat drying. The useful volatile basic substances include, for example, ammonia, monomethylamine or dimethylamine. The desorption or elution of proteins by these volatile basic substances can be carried out according to (1) method comprising adding the volatile basic substance directly to the cation exchanger, which has adsorbed the proteins, in the presence of water and dissolving or introducing the former into the latter by diffusion, etc., (2) method comprising mixing and contacting the volatile basic substance once dissolved in a suitable solvent such as water, etc. with the cation exchanger, which has adsorbed the proteins, (3) method comprising filling in a column the cation exchanger which has adsorbed the proteins, and pouring into the column a solution of the volatile basic substance, or (4) method comprising collecting the cation exchanger after the adsorption of the proteins, contacting said cation exchanger in the wet state with the volatile basic substance in a gaseous state by blowing thereby to once disengage the ionic bonds and desorb the proteins, and then contacting the cation exchanger with water thereby to elute the proteins. An almost proper amount of the volatile basic substance to be used for the desorption or elution, that is, the amount of the volatile basic substance to be contacted with the cation exchanger, can be calculated on the basis of the capacity of said cation exchanger. Generally, it is preferable to use the volatile basic substance in an amount equal to or more than the exchange capacity of the cation exchanger.

In the present invention, the cation exchanger used can be simply regenerated by washing the cation exchanger with an acid such as hydrochloric acid, etc. after the desorption or elution of the proteins, and can be used again.

The proteins eluted from the cation exchanger can be concentrated according to the so far well known method, for example, by concentration under reduced pressure or by heat concentration. Drying can be carried, if necessary, after the concentration, by heat drying, spray drying or lyophilization.

Applicable microbial cells are not specially restricted in the present invention. For example, the present invention is very effective for separating and purifying microbial cellular proteins of yeasts utlizing hydrocarbons as a carbon source, for example, the genera Candida, Pichia, Torulopsis, etc.; bacteria utilizing hydrocarbons as a carbon source, for example, the genera *Pseudomonas, Bacillus, Methanomonas, Micrococcus, etc.*; yeasts utilizing sugars, alcohols or organic acids as a carbon source, for example, the genera *Saccharomyces, Torulopsis, Hansenula, Rhodotorula*, etc.; bacteria utilizing the sugars, alcohols or organic acids *Escherichia, Aerobacter*, etc.

The present invention is effective for separating and purifying the dissolved proteins, and therefore a method for extracting proteins from microbial cells or a method for removing impurities before or after the extraction is not especially restricted in the present invention.

Now, the present invention will be explained in detail by way of examples.

EXAMPLE 1

1 kg of dry cells of *Candida lipolytica* is dipped in 4 l of 0.4 N hydrochloric acid in advance, and the resulting suspension is heated at 100° C for 20 minutes. Then, the resulting suspension is adjusted with an aqueous sodium hydroxide solution so that the final concentration of the suspension can take 0.75 N and the yeast concentration can take 15%. Then, the suspension is stirred for one hour, while keeping the temperature at 35° C, thereby to extract proteins from the cells. Then, water is added to the suspension until the yeast concentration takes 5%. Further, hydrochloric acid is added thereto til pH 7 thereby to neutralize the suspension. Then, the suspension is centrifuged, whereby 18.9 l of protein extract solution is obtained. Successively, the extract solution is passed through a gel filter column packed with a gel filtration medium, cross-linked dextran (Sephadex G-25, bead form, trademark of a product made by Pharmacia, Sweden) to remove salts or most of low-molecular weight substances, and 19 l of a solution containing high-molecular substances is obtained thereby. It is found by analysis that said solution containing high-molecular substance contains 0.42 kg of proteins and about 0.17 kg of polymer impurities such as polysaccharides. Concentrated hydrochloric acid is added to the solution containing high-molecular substances to adjust pH to 4.2, whereby isoelectric point precipitation of proteins is carried out. After the isoelectric point precipitation, 17 l of supernatant is separated by decantation. The supernatant contains 68 g of dissolved proteins that cannot be recovered by the isoelectric point precipitation. Then, hydrochloric acid is added to 17 l of said supernatant to adjust the pH to 3, and then 140 g (dry basis) of cation exchanger beads of sulfonic acid-type, cross-linked dextran system, activated to H+ form (SP-Sephadex, trademark of a product made by Pharmacia, Sweden; particle sizes: 40 to 120 μ) is added thereto, and stirred for a short time. Then, the supernatant is removed by filtration by means of suction. Then, said cation exchanger beads that have adsorbed the proteins are washed with a small amount of water, and then admixed with 0.5 N ammonia water in a capacity equal to that of said cation exchanger thereby to elute the proteins from the beads. After the protein elution the cation exchanger beads are separated by filtration, whereby a purified protein solution is obtained. The cation exchanger beads thus separated are washed with a small amount of water, and the washing effluent is added to said purified protein solution. Then, said purified protein solution is concentrated under reduced pressure to remove ammonia, and then lyophilized, whereby 61 g of the desired purified protein powders having a purity of 91% is obtained. In this case, the protein recovery is 82%.

In this Example 1, the drying can be also easily carried out by spray drying, and in that case the ammonia can be removed at the same time.

Further, when the ammonia water containing excess ammonium ions in a capacity in excess of the exchange capacity of the cation exchanger beads is used at the elution of proteins from the cation exchanger beads, the ammonia water solution containing eluted proteins can be used again, as it is, as the protein-eluting agent after the elution of proteins, and in that case, the proteins can be considerably concentrated, which is very favourable for the process.

EXAMPLE 2

118 g of dry cells of petroleum-utilizing yeasts, *Candida lipolytica*, is used. Protein extraction, neutralization, gel filtration and isoelectric point precipitation are carried out in the same manner as in Example 1, whereby most of proteins is recovered and 2 l of the remaining supernatant is obtained. The supernatant contains 8.0 g of dissolved proteins that cannot be recovered by the isoelectric point precipitation. The resulting protein solution is poured into a chromatographic glass tube having a diameter of 3 cm and a length of 17 cm, packed with 20 g (dry basis) of phosphoric acid-type cellulose ion exchanger beads, activated to H+ form (PPM Cellulose, trademark of a product made by Brown Co., USA; particle sizes: 5 to 25 μ) thereby to adsorb proteins. Other impurities than proteins, such as polysaccharides, are made to flow from the bottom of the glass tube. Then, 150 cc of water is poured into said glass tube to wash the beads, and then 500 cc of ammonia gas is passed through said glass tube from the top downwards at a rate of 100 cc/min under about one atmosphere from a cylinder provided with a gas flow meter thereby to desorb the proteins from the beads. Successively, 100 cc of water is poured into the glass tube from the top of the glass tube to elute the proteins, whereby 98 cc of a dilute aqueous ammonia solution containing the proteins is obtained from the bottom of the glass tube. Then, the resulting protein solution is concentrated under reduced pressure to remove the ammonia therefrom, and the concentration is continued until the entire volume reaches 30 cc. Then, the concentrate is lyophilized, whereby 8.1 g of the desired purified white protein powders having a purity of 93% is obtained. Protein recovery: 94%

EXAMPLE 3

100 g of cells of *Candida lipolytica* are treated in the same manner as in Example 1, and hydrochloric acid is added to 1.9 l of solution of high molecular weight fraction resulting from the gel filtration. Isoelectric point precipitation starts to take place at a pH of about 6. When the hydrochloric acid is continued to add until pH 3, the precipitates starts to be dissolved again, whereby a clear protein solution is obtained. Then, said protein solution (protein content: 41.8 g) is subjected to pH adjustment, adsorption by the cation exchanger, elution by ammonia water, concentration under reduced pressure and lyophilization in the same manner as in Example 1, whereby 34.2 g of the desired purified protein having a purity of 92% is obtained. Protein recovery: 75%.

As is apparent from this Example 3, the protein, which can be precipitated by the isoelectric point precipitation, though the precipitates can be dissolved again under strongly acidic conditions, can be effectively separated and purified according to the present invention.

EXAMPLE 4

Separation and purification of proteins are carried out in the same process as described in Example 1 or 2, changing the species of the microbial cells. The results are given in the following table.

Table

| Microbial cell species | Process | Purity (%) | Protein recovery (%) | Color |
| --- | --- | --- | --- | --- |
| Torulopisis sp. | Ex. 1 | 87 | 95 | white |
| Torula sp. | Ex. 1 | 85 | 93 | high yellowish brown |
| Saccharomyces cerevisiae | Ex. 2 | 92 | 90 | white |
| Pseudomonas sp. | Ex. 2 | 90 | 92 | white |
| Aerobacter sp. | Ex. 2 | 88 | 90 | white |

EXAMPLE 5

100 g of wet cells of baker's yeast, Saccharomyces cerevisiae (dry basis: 25 g) is admixed with 3 ml of an aqueous 30% sodium hydroxide solution and 148 ml of water to prepare a slurry having a pH of 11. The resulting slurry as placed in a 1 l autoclave, and the autoclave is dipped in an oil bath while stirring the slurry. The autoclave is elevated to 170° C, and kept at the temperature for 5 minutes thereby to extract proteins. Then, the autoclave is immediately dipped in running water to cool it to 40° C within 5 minutes. Then, the slurry is centrifuged to remove the extraction residue, and 164 ml of a protein extract solution is obtained thereby. The protein extract solution has a pH of 9.5 and a protein content of 6.9 g. A very small amount of concentrated hydrochloric acid is added to the protein extract solution to adjust the pH to 3.2. At that time, the proteins start to precipitate at a pH of about 6.0, but the resulting precipitates are dissolved again at a pH of 3.5. The extract solution is poured into a chromatographic glass tube column having a diameter of 3 cm and a length of 8 cm, packed with 50 g (dry basis) of sulfoethyl cellulose activated to $H^+$ form (SE-cellulose, trademark of a product made by Serva, Germany; particle sizes: 5 to 25 $\mu$), from the top of the column thereby to adsorb the proteins, and the resulting filtrate is made to flow from the bottom of the column, and separated. Then, 50 ml of water is passed through the column to wash the powders, and then immediately 100 ml of 1 N ammonia water is poured into the column thereby to elute the proteins adsorbed on said cation exchanger powders, and a protein solution is collected at the bottom of the column. On the other hand, the column is washed with 50 ml of water, and the washing effluent is added to said protein solution. Then, the protein solution is concentrated under reduced pressure, and lyophilized, whereby 7 g of the desired, light yellow proteins having a purity of 90.5% are obtained. Protein recovery 92%.

EXAMPLE 6

100 g of dry cells of petroleum-utilizing yeast, Candida lipolytica, is dipped in 900 ml of an aqueous 0.4% sodium hydroxide solution, and the pH of the suspension is adjusted to 12.0. Then, the suspension is placed in a 1 autoclave, and elevated to 150° C over a period of 27 minutes, while stirring the suspension, and kept at that temperature for 5 minutes thereby to extract proteins. Then, the suspension is cooled, and an extract solution is obtained by centrifugal separation. The resulting extract solution has a pH of 10.5. Then, 760 ml of the extract solution is admixed with 6 g (dry basis) of strong cation exchange resin activated to $H^+$ form (Dowex 50 WX 8, trademark of a product made by Dow Chemical Co., USA) to remove low molecular weight substances, and sufficiently stirred and left standing for 5 minutes, whereby sodium ions, and organic low molecular weight cations such as those of amino acids, etc. are removed. As a result, the pH of the solution reaches 5.0, and a portion of the proteins is precipitated. The resulting protein precipitates and paid cation exchange resin are separated by centrifuge, whereby 850 ml of the remaining protein solution (protein content: 7 g) is obtained. A small amount of hydrochloric acid is added to the protein solution to adjust the pH to 4.0, and then 20 g of sulfoethylated, cross-linked dextran beads activated to $H^+$ form (SE-sephadex trademark of a product made by Pharmacia, Sweden; particle size: 40 to 120 $\mu$) is added thereto as a cation exchanger. The solution is left standing for 5 minutes to adsorb the proteins. Then, the cation exchanger that has adsorbed the proteins is filtered off, washed with 100 ml of water, and then admixed with 100 ml of 0.5 N ammonia water to elute the adsorbed proteins. After the elution of the proteins, the cation exchanger is filtered off, and washed with 50 ml of water. The washing effluent is added to said protein solution. Then, the protein solution is concentrated under reduced pressure, and then lyophilized, whereby 7.1 g of white, purified proteins having a purity of 92% is obtained. Protein recovery 94%.

What is claimed is:

1. A process for recovering with high purity substantially all of the different microbial cellular proteins having different physico-chemical properties from a solution obtained by extracting microbial cells with an aqueous extraction solution, comprising (1) contacting the solution with a strong cation exchanger at a pH value of less than 4.5 thereby adsorbing the proteins onto said cation exchanger, the cation exchanger being sufficiently swollen by water so that ions of the proteins can easily arrive at exchanging groups present in the cation exchanger, and (2) desorbing the proteins adsorbed by said strong cation exchanger by contacting said cation exchanger with a volatile basic substance in the presence of water to thereby recover substantially all of said different proteins with high purity.

2. A process for separating with high purity substantially all of the different microbial cellular proteins having different physico-chemical properties from a solution obtained by extracting microbial cells with an aqueous extraction solution, comprising contacting the solution with a strong cation exchanger at a pH value of less than 4.5 thereby adsorbing the proteins onto said cation exchanger, the cation exchanger being sufficiently swollen by water so that ions of the proteins can easily arrive at exchanging groups present in the cation exchanger, contacting the cation exchanger containing adsorbed proteins with a volatile basic substance in the presence of water so that the proteins are desorbed or eluted and an eluate containing the proteins is formed, and removing the volatile basic substance from said eluate by evaporation.

3. The process according to claim 2, wherein said strong cation exchanger is selected from the group consisting of sulfonated cellulose, phosphorylated cellulose, sulfonated dextran, phosphorylated dextran, sulfonated polyacrylamide and phosphorylated polyacrylamide.

4. The process according to claim 3, wherein said strong cation exchanger is granular in form.

5. The process according to claim 2, wherein said volatile basic substance is ammonia, monomethylamine or dimethylamine.

6. The process according to claim 2, wherein the amount of volatile basic substance contacted with said strong cation exchanger is at least equal to the exchange capacity of the cation exchanger.

7. The process according to claim 2, wherein the amount of volatile basic substance contacted with said strong cation exchanger is greater than the exchange capacity of the cation exchanger whereby the eluate produced by desorbing contains a quantity of said volatile basic substance, said process further comprising contacting another aqueous solution containing dissolved proteins with said strong cation exchanger to adsorb proteins thereon, and thereafter desorbing the proteins adsorbed by said strong cation exchanger by contacting said cation exchanger with said eluate.

8. The process according to claim 2, wherein the adsorption of the proteins is carried out at a pH of less than 3.5.

9. The process according to claim 2, wherein the microbial cellular proteins are of yeasts utilizing hydrocarbons as a carbon source, bacteria utilizing hydrocarbons as a carbon source, yeasts utilizing sugars, alcohols or organic acids as a carbon source or bacteria utilizing sugars, alcohols or organic acids as a carbon source.

10. A process for recovering with high purity substantially all of the different microbial cellular proteins having different physico-chemical properties contained in microbial cells comprising treating the microbial cells with an aqueous extracting solution so as to dissolve the different microbial cellular proteins contained in the microbial cells into the solution; contacting said solution containing the dissolved microbial cellular proteins with a strong cation exchanger at a pH value of less than 4.5, said cation exchanger being sufficiently swollen by water so that ions of said proteins can easily arrive at exchanging groups present in said cation exchanger, desorbing the proteins adsorbed by said cation exchanger by contacting said cation exchanger with a volatile basic substance; and separating the basic substance from said proteins by evaporation.

11. The process according to claim 10, wherein said strong cation exchanger is selected from the group consisting of sulfonated cellulose, phosphorylated cellulose, sulfonated dextran, phosphorylated dextran, sulfonated polyacrylamide and phosphorylated polyacrylamide.

12. The process according to claim 11, wherein said strong cation exchanger is granular in form.

13. The process according to claim 10, wherein said volatile basic substance is ammonia, monomethylamine or dimethylamine.

14. The process according to claim 10, wherein the amount of volatile basic substance contacted with said strong cation exchanger is at least equal to the exchange capacity of the cation exchanger.

15. The process according to claim 10, wherein the amount of volatile basic substance contacted with said strong cation exchanger is greater than the exchange capacity of the cation exchanger whereby the eluate produced by desorbing contains a quantity of said volatile basic substance, said process further comprising contacting another aqueous solution containing dissolved proteins with said strong cation exchanger to adsorb proteins thereon, and thereafter desorbing the proteins adsorbed by said strong cation exchanger by contacting said cation exchanger with said eluate.

16. The process according to claim 10, wherein the adsorption of the proteins is carried out at a pH of less than 3.5.

17. A process according to claim 10, wherein the microbial cellular proteins are of yeasts utilizing hydrocarbons as a carbon source, bacteria utilizing hydrocarbons as a carbon source, yeasts utilizing sugars, alcohols or organic acids as a carbon source or bacteria utilizing sugars, alcohols or organic acids as a carbon source.

18. A process for recovering with high purity substantially all the different microbial cellular proteins having different physico-chemical properties contained in microbial cells which comprises treating the microbial cells with an aqueous extracting solution so as to form a suspension of said microbial cells in said solution and cause the different microbial cellular proteins contained in the microbial cells to dissolve into said solution; separating said solution from said suspension so that an extract solution containing said different microbial cellular proteins therein is obtained; contacting the extract solution with a strong cation exchanger at a pH value of less than 4.5, said cation exchanger being sufficiently swollen by water so that ions of said proteins can easily arrive at exchanging groups present in said cation exchanger; desorbing the proteins adsorbed by said cation exchanger by contacting said cation exchanger with a volatile basic substance; and separating the basic substance from said proteins by evaporation.

19. The process according to claim 18, wherein said strong cation exchanger is selected from the group consisting of sulfonated cellulose, phosphorylated cellulose, sulfonated dextran, phosphorylated dextran, sulfonated polyacrylamide and phosphorylated polyacrylamide.

20. The process according to claim 19, wherein said strong cation exchanger is granular in form.

21. The process according to claim 18, wherein said volatile basic substance is ammonia, monomethylamine or dimethylamine.

22. The process according to claim 18, wherein the amount of volatile basic substance contacted with said strong cation exchanger is at least equal to the exchange capacity of the action exchanger.

23. The process according to claim 18, wherein the amount of volatile basic substance contacted with said strong cation exchanger is greater than the exchange capacity of the cation exchanger whereby the eluate produced by desorbing contains a quantity of said volatile basic substance, said process further comprising contacting another aqueous solution containing dissolved proteins with said strong cation exchanger to adsorb proteins thereon, and thereafter desorbing the proteins adsorbed by said strong cation exchanger by contacting said cation exchanger with said eluate.

24. The process according to claim 18, wherein the adsorption of the proteins is carried out at a pH of less than 3.5.

25. The process according to claim 18, wherein the microbial cellular proteins are of yeasts utilizing hydrocarbons as a carbon source, bacteria utilizing hydrocarbons as a carbon source, yeasts utilizing sugars, alcohols or organic acids as a carbon source or bacteria utilizing sugars, alcohols or organic acids as a carbon source.

26. The process of claim 1, wherein said solution obtained by the extracting microbial cells contains polysaccharides.

27. The process of claim 2, wherein said solution obtained by the extracting microbial cells contains polysaccharides.

28. The process of claim 10, wherein the solution dissolved cellular proteins further contains polysaccharides.

29. The process of claim 18, wherein said extract solution further contains polysaccharides.

30. A process for separating with high purity substantially all of the different microbial cellular proteins having different physico-chemical properties from a solution obtained by extracting microbial cells with an aqueous solution to form an extract solution containing salts, low molecular weight substances, and high molecular weight substances including said proteins and polysaccharides, and thereafter treating said extract solution to remove said salts and low molecular weight substances therefrom and thereby produce an extract composition comprising an aqueous solution of said proteins and polysaccharides; said process comprising contacting said extract composition with a strong cation exchanger at a pH value of less than 4.5 thereby adsorbing the proteins onto said cation exchanger, said cation exchanger being sufficiently swollen by water so that ions of the proteins can easily arrive at exchanging groups present in the cation exchanger, contacting the cation exchanger containing adsorbed proteins with a volatile basic substance in the presence of water so that the proteins are desorbed or eluted and an eluate containing the proteins is formed, and removing the volatile basic substance from said eluate by evaporation.

31. The process of claim 30 further comprising adjusting the pH of said extract composition to the isoelectric point of the proteins therein to cause isoelectric precipitation of some of the proteins in said extract composition and thereafter removing the proteins so precipitated from said extract composition prior to contacting said extract composition with said strong cation exchanger.

32. The process of claim 30 wherein the microbial cellular proteins are of yeasts utilizing hydrocarbons as a carbon source, bacterial utilizing hydrocarbons as a carbon source, yeasts utilizing sugars, alcohols or organic acids as a carbon source or bacteria utilizing sugars, alcohols or organic acids as a carbon source.

33. Process for recovering with high purity substantially all of different microbial cellular proteins having different physico-chemical properties contained in microbial cells which comprises treating the microbial cells with an aqueous extracting solution so as to form a suspension of said microbial cells in said solution and cause dissolution into said aqueous extracting solution of (1) salts, (2) low molecular weight substances, and (3) high molecular weight substances composed of different microbial cellular proteins and polysaccharides separating said aqueous extracting solution from said suspension to produce an extract solution containing said salts, said low molecular weight substances and said high molecular weight substances; contacting said extract solution with a strong cation exchanger at a pH value of less than 4.5, said cation exchanger being sufficiently swollen by water so that ions of said proteins can easily arrive at exchanging groups present in said cation exchanger; desorbing the proteins adsorbed by said cation exchanger by contacting said cation exchanger with a volatile basic substance; and separating the basic substance from said proteins by evaporation.

34. The process of claim 33 further comprising adjusting the pH of said extract composition to the isoelectric point of the proteins therein to cause isoelectric precipitation of some of the proteins in said extract composition and thereafter removing the proteins so precipitated from said extract composition prior to contacting said extract composition with said strong cation exchanger.

35. The process of claim 33 wherein the mircobial cellular proteins are of yeasts utilizing hydrocarbons as a carbon source, bacteria utilizing hydrocarbons as a carbon source, yeasts utilizing sugars, alcohols or organic acids as a carbon source or bacteria utilizing sugars, alcohols or organic acids as a carbon source.

* * * * *